United States Patent [19]

Gallopo et al.

[11] Patent Number: 5,077,051

[45] Date of Patent: Dec. 31, 1991

[54] SUSTAINED RELEASE OF ACTIVE AGENTS FROM BIOADHESIVE MICROCAPSULES

[75] Inventors: Andrew R. Gallopo, Garfield; Steven S. Dills, Hackettstown, both of N.J.

[73] Assignee: Warner-Lambert Company, Morris Plains, N.J.

[21] Appl. No.: 508,216

[22] Filed: Apr. 10, 1990

[51] Int. Cl.$^5$ ............................................ A61F 13/00
[52] U.S. Cl. .................................. 424/435; 424/76.3; 424/485; 424/489; 424/497
[58] Field of Search ............... 424/485, 489, 435, 76.3, 424/497

[56] References Cited

U.S. PATENT DOCUMENTS

| | | | |
|---|---|---|---|
| 2,809,916 | 10/1957 | Hermelin | 424/489 |
| 4,259,315 | 3/1981 | Lippmann | 424/459 |
| 4,695,467 | 9/1987 | Uemura | 424/489 |
| 4,795,436 | 1/1989 | Robinson | 514/457 |
| 4,800,087 | 2/1989 | Mehta | 424/497 |
| 4,812,444 | 3/1989 | Mitsuhashi | 514/777 |
| 4,876,097 | 10/1989 | Autant | 424/438 |
| 4,894,239 | 2/1990 | Noromura | 424/469 |
| 4,906,488 | 3/1990 | Pera | 424/76.3 |

*Primary Examiner*—Thurman K. Page
*Assistant Examiner*—William E. Benston
*Attorney, Agent, or Firm*—Carl W. Battle

[57] ABSTRACT

Bioadhesives microcapsules capable of sustained release comprise xanthan gum, locust bean gum, a bulking agent and an active agent. The microcapsules are particularly useful for delivering buffering agents to the oral cavity for anticaries purposes.

12 Claims, No Drawings

SUSTAINED RELEASE OF ACTIVE AGENTS FROM BIOADHESIVE MICROCAPSULES

BACKGROUND OF THE INVENTION

1. Field of the Invention

The present invention relates to the sustained release of active agents, and particularly to novel bioadhesive microcapsules which permit the sustained release of active agents such as therapeutic or cosmetic agents into, for example, the oral cavity.

2. Description of the Prior Art

The introduction of active agents into the oral cavity or other physical location by sustained release has the advantage of reducing the number of times an active agent must be administered each day, and further provides a uniform distribution of the active agent over an extended period of time.

Conventionally, medicinal agents are either coated to a particular thickness with a relatively insoluble material, or they are embedded into a rigid lattice of resinous material. In this way, the medicinal agent is continuously made available for absorption into the blood stream to replace the amount of drug eliminated while the dosage form is passing through the patient's gastrointenstinal system.

For example, U.S. Pat. No. 4,610,870 discloses an orally ingested coated tablet having a controlled release formulation which is said to provide for substantially zero order release of medicaments over a 10 to 12 hour period. The controlled release formulation of this patent includes a core containing the medicament, one or more water-soluble hydrocolloid gelling agents having a viscosity of 10,000-200,000 centipoises, and additional binders, lubricants and anti-adherents.

U.S. Pat. No. 3,911,099 provides long-acting capsules or tablets for introducing medications onto the oral cavity. This patent also briefly mentions the possibility of incorporating anti-caries and anti-plaque agents into the tablets and micro-capsules provided.

U.S. Pat. No. 3,623,997 is directed to a process of treating the walls of a controlled release capsule with an organic solvent solution of waxy material.

U.S. Pat. No. 4,698,264 discloses a solid, water-dispersible delayed-release particulate composition which consists of a matrix composed of a poorly water soluble salt, and an active ingredient insoluble in and uniformly distributed through the matrix.

The above-described efforts, while providing usable sustained release compositions, generally are not fully acceptable in one or more respects. For example, some individuals find tablet forms to be difficult to swallow, or if the agent is to be delivered to the oral cavity, tablet forms are inconvenient to use or possess undesirable textural properties. Prior micro-capsule sustained release forms often have these deficiencies or further lack properties which would make them suitable for delivery to the oral cavity, such as adhesiveness.

It is therefore generally agreed that there presently is no completely satisfactory means for delivering an active agent to the oral cavity by sustained release. As noted above, it would be particularly desirable to devise an effective sustained release system for delivering an active agent, such as an anti-caries agent, to the oral cavity.

The process of dental caries formation is initiated by the production of acid metabolic end products by the plaque bacteria from dietary carbohydrates. The incidence and rate of caries formation is a function of the frequency of ingestion of cariogenic carbohydrates and of personal oral hygiene habits. Plaque removal by mechanical means and with antiplaque mouthrinses and use of fluoride in dentrifices, mouthrinses, and drinking water are conventionally used to impede the caries formation process. Recently, Warner-Lambert has provided evidence that chewing Trident Gum following carbohydrates ingestion also inhibits caries formation. Trident functions by increasing salivary flow which, in turn, elevates plaque pH by washing the acid end products away. Saliva also contains buffers, particularly bicarbonate, which neutralize plaque acids.

It would be highly desirable to augment the buffering capacity of saliva by supplying buffering agents to the oral cavity. In order for such buffering agents to exert a therapeutic benefit, these exogenous buffers would have to be provided in a controlled release dosage form which would allow the buffer to be released over a prolonged period of time, and the buffering agents would need to be provided in a dosage form which would be adhesive to the oral cavity, to prevent their rapid clearance from the oral cavity by salivary action.

SUMMARY OF THE INVENTION

Accordingly, the present invention provides bioadhesive microcapsules which permit the sustained release of active agents such as therapeutic or cosmetic agents. A preferred application of the invention is the provision of bioadhesive microcapsules containing buffering agents, which may be delivered by sustained release into the oral cavity, to prevent caries formation.

Generally, the present invention contemplates two compositions of matter directed to related forms of bioadhesive microcapsule formulations.

According to a first composition, a composition of matter comprising bioadhesive microcapsules is provided, the bioadhesive microcapsules comprising xanthan gum, locust bean gum, a bulking agent and an active agent.

According to a second composition, a composition of matter comprising bioadhesive microcapsules is provided, said microcapsules comprising ethylcellulose and an active agent.

The invention also contemplates methods for preparing the subject novel bioadhesive microcapsules.

In accordance with a first method, bioadhesive microcapsules capable of the sustained release of an active agent are prepared by a process which comprises:

(a) providing a hot aqueous solution or suspension of an active agent;

(b) adding xanthan gum, locust beam gum and a bulking agent to said aqueous solution, to form a viscous solution;

(c) cooling said viscous solution;

(d) drying said viscous solution, to form a solid material containing said active agent;

(e) forming said solid material into bioadhesive microcapsules; and (f) recovering said bioadhesive microcapsules.

In accordance with a second method of preparation, bioadhesive microcapsules capable of the sustained release of an active agent are prepared by a process which comprises:

(a) providing an aqueous solution or suspension comprising an active agent and ethylcellulose;

(b) drying said aqueous solution or suspension to form a solid material containing said active agent;

(c) forming said solid material into bioadhesive microcapsules; and (d) recovering said microcapsules.

In accordance with a third method of preparation, bioadhesive microcapsules capable of the sustained release of an active agent are prepared by a process which comprises:

(a) providing a hot aqueous solution or suspension of an active agent;

(b) adding xanthan gum, locust bean gum and a bulking agent to said aqueous solution, to form a viscous solution;

(c) spray drying said viscous solution, to form a bioadhesive microcapsules; and (d) recovering said bioadhesive microcapsules.

DETAILED DESCRIPTION OF THE INVENTION

Applicants have unexpectedly provided a composition of matter comprising bioadhesive microcapsules, said microcapsules comprising xanthan gum, locust bean gum, a bulking agent and an active agent.

This first composition provided by the present invention is advantageously composed entirely of food grade materials, and the composition provides a sustained release of an active agent over an extended period of time.

Xanthan gum, the primary adhesive of the presently disclosed microcapsules, is a commercially available synthetic water-soluble biopolymer made by the fermentation of carbohydrates. Xanthan gum is heat-stable and exhibits a good tolerance for strongly acid and basic solutions. Xanthan gum also possesses good mouth feel characteristics. The first composition of the invention utilizes xanthan gum in combustion with locust bean gum.

Locust bean gum, also known as carob-seed gum, is a commercially available polysaccharide plant mucilage which is essentially composed of galactomannan (carbohydrate). Locust bean gum is known to exhibit a synergistic effect when combined with xanthan gum, thereby yielding a stronger gel when prepared in accordance with the present invention.

The xanthan and locust bean gums employed in accordance with the first composition of the invention are preferably utilized in approximately equal amounts. In this regard, a commercially available 50/50% mixture of xanthan gum and locust bean gum is conveniently employed, available from Kelco (San Diego, CA) under the trademark Kelgum.

The bulking agent employed may be selected from a wide variety of known bulking agents, including those selected from the groups consisting of gelatin, hydrocolloids glycerin, microcrystalline cellulose, methylcellulose, polyvinylpyrrolidone (PVP), sodium carboxymethylcellulose and whey solids. Gelatin is the preferred bulking agent employed, since it is both adhesive and water soluble.

The present invention provides for the encapsulation and sustained release of a wide variety of active agents, including those selected from the group consisting of therapeutic agents, cosmetic agents and mixtures thereof.

In a preferred aspect of the invention, the active agent comprises a therapeutic agent such as a buffering agent, which is delivered into the oral cavity by means of the bioadhesive microcapsules of the invention, in order to prevent the formation of caries.

Suitable buffering agents include those selected from the group consisting of potassium phosphate dibasic, calcium carbonate, sodium potassium dibasic, sodium bicarbonate, ammonium bicarbonate, potassium carbonate, magnesium carbonate, calcium phosphate tribasic, sodium sesquicarbonate, ammonium carbonate, tetrasodium pyrophosphate, calcium hydroxide, sodium hydroxide, potassium hydroxide and mixtures thereof.

Generally, the buffering agent should comprise a basic salt in an amount sufficient to neutralize approximately 10 mg of lactic acid. Lactic acid is the acid challenge of choice against the basic salts, since it is produced by the fermentation of carbohydrates. Ten mg of lactic acid was selected as the challenge based upon the following calculations. A stick of chewing gum weighs approximately 3 g and is about 75% carbohydrate. Cariogenic plaque metabolizes sucrose to lactic acid with 36% of the sucrose being converted to lactic acid. Assuming that only 1% of the sucrose is metabolized with the remainder being swallowed, then 8.1 or approximately 10 mg of lactic acid remain as the challenge.

The stoichiometry of the reaction of potassium phosphate dibasic and lactic acid may be determined by titration to require a mole ratio of $K_2HPO_4$ to lactic acid of 2:1.

The first composition of the invention may be optionally coated with a food grade wax, in order to improve the sustained release characteristics of the microcapsules. The waxes useful in the invention comprise both natural and synthetic waxes and include without limitation animal waxes such as beeswax, lanolin and shellac wax, vegetable waxes such as carnauba, candelilla, sugar cane and bayberry wax, mineral waxes such as petroleum waxes including paraffin and microcrystalline wax. The wax coating may be formed on the microcapsules by known methods, such as hot melt or granulation procedures. Granulation is the preferred coating procedure, and carnauba wax is preferably employed as the wax coating material for all of the wax coated compositions of the invention. The wax coating may optionally include calcium carbonate, in order to fill channels in the wax coating to provide greater sustained release, and also to serve as a second source of acid consuming power.

The present invention also contemplates a second composition of matter comprising bioadhesive microcapsules, the microcapsules comprising ethylcellulose and an active agent.

Ethylcellulose is a commercially available ethyl ether of cellulose which has been unexpectedly found to function as an effective sustained release bioadhesive agent when formed into microcapsules in accordance with the invention.

The second composition of the invention includes an active agent which may be selected from the group consisting of therapeutic agents, cosmetic agents and mixtures thereof.

The second composition of the invention does not require a bulking agent, although one may be employed if desired.

The active agent utilized in the second composition of the invention preferably comprises a therapeutic agent, which most preferably comprises a buffering agent. Useful buffering agents again may be selected from the group consisting of potassium phosphate dibasic, calcium carbonate, sodium potassium dibasic, sodium bicarbonate, ammonium bicarbonate, potassium carbonate, magnesium carbonate, calcium phosphate tribasic, sodium sesquicarbonate, ammonium carbonate, tetrasodium pyrophosphate, calcium hydroxide, sodium hydroxide, potassium hydroxide and mixtures thereof.

As with the first composition, the second composition of the invention may be provided with a wax coating in order to enhance the sustained release characteristics of the bioadhesive microcapsules. Carnauba wax is again preferred, with usable waxes being selected from the group consisting of animal waxes, vegetable waxes, mineral waxes, synthetic waxes and mixtures thereof.

The bioadhesive microcapsule compositions provided by the invention may generally be incorporated into any suitable delivery system known in the art. Exemplary delivery systems include gels, center-filled chewing gums and pressed mints. Generally, the delivery system may be appropriately selected depending upon the physical location the microcapsules are to be delivered to, as well as the intended use of the microcapsules. The above-described exemplary delivery systems are preferred in accordance with the present invention, since they permit effective delivery of the bioadhesive microcapsules into the oral cavity.

The invention also contemplates three methods for preparing the novel bioadhesive microcapsules of the invention.

In accordance with a first method of preparation, bioadhesive microcapsules capable of the sustained release of an active agent are prepared by a process which comprises:

(a) providing a hot aqueous solution or suspension of an active agent;

(b) adding xanthan gum, locust bean gum and a bulking agent to said aqueous solution, to form a viscous solution;

(c) cooling said viscous solution;

(d) drying said viscous solution, to form a solid material containing said active agent;

(e) forming said solid material into bioadhesive microcapsules; and (f) recovering said bioadhesive microcapsules.

Preferably, the drying of the viscous solution according to the first method is accomplished by lyophilizing techniques well known in the art. Microwave and conventional drying methods known in the art may also be employed.

The solid material produced by the drying procedure may be formed into microcapsule form by methods known to those skilled in the art, such as by breaking the solid material into pieces, followed by milling and sieving the pieces into microcapsules.

Suitable active agents and bulking agents follow in accordance with the above-described first composition of the invention, with potassium phosphate dibasic and gelatin being preferred, respectively.

The addition of the xanthan gum, locust bean gum and bulking agent to the aqueous solution is preferably accompanied by vigorous stirring of the aqueous solution, to facilitate dissolving of these components.

Also preferably, the viscous solution of xanthan gum, locust bean gum and active agent should be cooled to approximately room temperature, prior to drying the viscous solution.

In accordance with the first method of the invention, the bioadhesive microcapsules may optionally be coated with wax to enhance the sustained release properties of the microcapsules.

Usable waxes include those selected from the group consisting of animal waxes, vegetable waxes, mineral waxes, synthetic waxes and mixtures thereof, with carnauba wax being preferred.

The preferred process of wax coating utilized in accordance with the first method of the invention comprises a hot melt procedure, well known to those skilled in the art.

Further, calcium carbonate may be optionally added to the hot melt wax composition, prior to coating the bioadhesive microcapsules.

The first method of preparation also optionally includes a final step of incorporating the bioadhesive microcapsules produced into a suitable delivery system, such as a gel, a center-filled chewing gum or a pressed mint.

According to a second method of the invention, bioadhesive microcapsules capable of the sustained release of an active agent are prepared by a process which comprises:

(a) providing an aqueous solution or suspension comprising an active agent and ethylcellulose;

(b) drying said aqueous solution or suspension, to form a solid material containing said active agent;

(c) forming said solid material into bioadhesive microcapsules; and (d) recovering said microcapsules.

The drying step performed in accordance with the second method of the invention may consist of any known drying process, but preferably comprises forming a film of the aqueous solution or suspension and subsequently allowing the aqueous solution or suspension to dry, to form a solid material containing the active agent.

According to the second method, the solid material is preferably formed into microcapsule form by milling and sieving techniques known in the art.

Again, useful active agents may generally be chosen from therapeutic and/or cosmetic agents, and preferably comprise buffering agents, such as those selected from the group consisting of potassium phosphate dibasic, calcium carbonate, sodium potassium dibasic, sodium bicarbonate, ammonium bicarbonate, potassium carbonate, magnesium carbonate, calcium phosphate tribasic, sodium sesquicarbonate, ammonium carbonate, tetrasodium pyrophosphate, calcium hydroxide, sodium hydroxide, potassium hydroxide and mixtures thereof.

The ethylcellulose based bioadhesive microcapsules prepared in accordance with the second method of the invention may optimally be coated with a wax selected from the group consisting of animal waxes, vegetable waxes, mineral waxes, synthetic waxes and mixtures thereof. Carnauba wax is again preferred.

The second method of the invention also contemplates the optional incorporation of the microcapsules into a delivery system, such as a gel, center-filled chewing gum or a pressed mint, as appropriate.

According to a third method of preparation, bioadhesive microcapsules capable of the sustained release of an active agent are prepared by a process which comprises:

(a) providing a hot aqueous solution or suspension of an active agent;

(b) adding xanthan gum, locust bean gum and a bulking agent to said aqueous solution, to form a viscous solution;

(c) spray drying said viscous solution, to form bioadhesive microcapsules; and (d) recovering said bioadhesive microcapsules.

The above-described third method of the invention comprises the preferred process for preparing the first compositions of the invention in a production scale operation.

In a particularly preferred aspect of the third method of the invention, the microcapsules are coated with a wax by a granulation technique. Suitable waxes again may be selected from the group consisting of animal waxes, vegetable waxes, mineral waxes, synthetic waxes and mixtures thereof. Carnauba wax is preferably employed, if a wax coating is to be utilized.

The temperature of the solution or suspension formed in accordance with the third method is preferably maintained at approximately 70°-90° C., thus eliminating the necessity of cooling the solution/suspension prior to drying.

Suitable active agents and bulking agents follow in accordance with the first method of preparation, and the first compositions, of the invention. Preferably, the active agent again comprises a buffering agent such as potassium phosphate dibasic, and the bulking agent comprises gelatin. The resulting microcapsules produced exhibit a high degree of bioadhesiveness and sustained release characteristics, and these microcapsules may be conveniently loaded into a delivery system for delivery of the buffering agents into the oral cavity.

The spray drying technique employed in accordance with the third method is well known to those skilled in the food products art, and serves to dry finely divided droplets of the suspension/solution with minimal heat degradation of the final product.

The viscous solution formed according to the third method of the invention is preferably stirred vigorously in order to facilitate dissolution of the essential components.

Also, calcium carbonate is optionally added as a buffering agent core component of the microcapsules produced by the third method, or may be added to the optional wax coating.

The following examples are given to illustrate the invention, but are not deemed to be limiting thereof. All percentages given throughout the specification are based upon weight percent, unless otherwise indicated.

EXAMPLE 1

Preparation of Bioadhesive Microcapsules

This example illustrates the preparation of bioadhesive microcapsules according to the first method of the invention.

Microcapsules were prepared by first loading Kelgum/gelatin with potassium phosphate dibasic. This was accomplished by dissolving the potassium phosphate to 0.1 M in hot deionized water (65°-70° C.), followed by addition of 1% Kelgum (50% xanthan gum and 50% locust bean gum) and 4% gelatin (225 bloom) for bulk with vigorous mechanical stirring. This viscous solution was then poured into petri dishes, allowed to cool to room temperature, frozen, lyophilized to dryness, broken into pieces, milled, and sieved. The lyophilizer was the Virtis Unitrap II instrument, the mill was the CRC Micromill, and the sieve was the CSC Scientific sieve shaker. The final solid composition comprised by weight 1% Kelgum, 4% gelatin, 36.4% potassium phosphate dibasic, 16.7% calcium carbonate and 41.9% carnauba wax.

EXAMPLE 2

Preparation of Wax Coated Bioadhesive Microcapsules

The following example illustrates the preparation of wax coated bioadhesive microcapsules according to the first method of the invention.

Was coated microcapsules were prepared as follows:
1. Carbauna wax (20 g) was melted on a hot plate at 95°-100° C.;
2. Calcium carbonate (8 g) was added to the wax with mechanized stirring, and stirring was continued until the $CaCo_3$ was thoroughly mixed into the wax;
3. Kelgum/gelatin particles (100-200 mesh size) loaded with 0.1 M $K_2HPO_4$ (loading concentration of Kelgum 1% and gelatins 4%) were added to this mixture with continuous mechanized stirring. The temperature of the mixture was maintained no higher than 100° C. in order to avoid decomposition of the Kelgum/gelatin mixture, and the mixture was stirred until evenly distributed;
4. The hot melt was quickly poured onto a clear, hard surface and allowed to cool. After hardening, the resulting solid mass was broken into pieces, milled and sieved to a particle size appropriate for subsequent bioadhesion and dissolution experiments.

EXAMPLE 3

Preparation of Bioadhesive Microcapsules

The following example illustrates the preparation of bioadhesive microcapsules in accordance with the second method of the invention.

Microcapsules of ethylcellulose were prepared by dissolving $K_2HPO_4$ in an aqueous ethylcellulose solution, followed by forming a 50 mil film on a teflon plate and subsequently allowing the film to dry, prior to milling and sieving the resulting pieces into microcapsules.

BIOADHESION MEASUREMENTS

The microcapsules produced by the procedures of Examples 1 and 2 were subjected to bioadhesion measurements, following the technique outlined by J. R. Robinson in U.S. Pat. No. 4,615,697, with certain modifications.

The modifications included using a No. 1 rubber stopper adapted with a metal fixture and a 1 cm diameter circle of plastic, in order to carry out tissue-to-tissue adhesion measurements. Rabbit stomach tissue was employed for this purpose. Ten mg of material whose bioadhesion was to be measured was spread on the bottom tissue over the area of a circle of 1 cm diameter.

The rubber stopper (with tissue) was then lowered onto the lower tissue for exactly one minute and the force in grams required to separate the two pieces of tissue was measured.

The wax coated microcapsules prepared according to Example 2 were found to exhibit approximately equivalent tissue/tissue adhesiveness compared to the uncoated microcapsules of Example 1.

Carnauba wax particles along were found to decrease the adhesion below that obtained with no microcapsule compositions (wax coated or uncoated).

DISSOLUTION EXPERIMENTS

The bioadhesive microcapsules prepared in accordance with Examples 1-3 were subjected to dissolution experiments, in order to determine the relative sustained release properties of these compositions.

In vitro dissolution studies were carried out by using an initial acid challenge of 10 mg of lactic acid in 25 ml water or 25 ml of 2 millimolar HCl, adding the microcapsules, then measuring the increase in pH as a function of time. The samples were thermostated in a shaking water bath at 37° C. Measurements were usually carried out at time points of 0, 5, 10, 20, 30, 40, 60, 90, 120, 150, and 180 minutes. A Radiometer PHM 84 research pH meter was employed for pH measurements.

An IBM AT personal computer was used to graph the data with the graphics software packages of Lotus and/or Sigmaplot (Jandel Scientific, Sausalito, CA).

Dissolution studies with particles of xanthan gum, locust bean gum and gelatin loaded with $K_2HPO_4$ were carried out, and indicated that improvement in sustained release was desirable. Adhesive particles were prepared with carnauba wax, using the hot melt procedure previously described. These particles yielded improved performance, but additional improvement in sustained release properties was still desired.

Accordingly, calcium carbonate was added during the preparation of the particles in order to fill the channels in the wax to yield greater sustained release, as well as to serve as a second source of acid consuming power. Good sustained release characteristics were obtained with 100 and 200 mg of microcapsules.

A comparison study of dissolution experiments with calcium carbonate along, calcium carbonate plus potassium phosphate dibasic, and unloaded microcapsules was carried out. The unloaded microcapsules were found to contribute nothing to the pH increase. However, $CaCO_3$ was found to make a small contribution to the pH increase with sustained release, while the combination of $CaCO_3$ and $K_2HPO_4$ raised the pH to approximately 6.5 in two hours and exhibited significant sustained release.

The effect of mesh size on dissolution rates was also investigated. As anticipated, the smallest particle size yielded the fastest release rate.

Additional experiments were carried out to determine how further additions of acid effected the pH of a typical dissolution profile. Six one mg additions of lactic acid after the initial ten mg challenge were made. Each addition of acid immediately lowered the pH by about 0.5 unit with subsequent recovery before the next addition twenty minutes later. This experiment was carried out in order to determine if the pH could recover from an additional amount of acid, simulating the intake of additional sugar which would be metabolized to lactic acid.

Similar dissolution studies were also carried out on the ethylcellulose microcapsules loaded with $K_2HPO_4$. The acid challenge in these studies was 25 ml of $2 \times 10^{-3}$ M HCl. Good sustained release was obtained with 200 mg of microcapsules. The addition of 2 ml of $2 \times 10^{-3}$ M HCl during a typical dissolution study was carried out. The pH was found to drop immediately upon acid addition, but recovered later in the dissolution.

EXAMPLE 4

Preparation of Bioadhesive Microcapsules

The following example illustrates the preparation of bioadhesive microcapsules in accordance with the third method of the invention.

Microcapsules were prepared by first loading Kelgum/gelatin with potassium phosphate dibasic. This was carried out by dissolving potassium phosphate to 0.067 M in hot, deionized water followed by addition of 0.67% Kelgum and 2.7% gelatin (225 bloom) with vigorous mechanical stirring until uniform. Calcium carbonate was added that was 30% of the solids content. This was accomplished by premixing the calcium carbonate in 50 ml of deionized water ($-80°$ C.) and adding to the above solution with vigorous mechanical stirring. This solution/suspension was then spray dried on a Buchi 190 Mini Spray Dryer. The temperature was maintained at approximately 70°-90° C. during the entire operation. Optimal instrument settings were an inlet temperature of 130°-150° C., aspirator setting of 20, air flow setting of 400, and flow rate of 6-8 ml/minute. A yield of approximately 35-40% was obtained based on the solids content of the solution/suspension. The resulting product was white, fluffy powder that was micro-sized. The resulting spray-dried particles comprised by weight 10.4% Kelgum, 41.8% gelatin, 17.8% potassium phosphate dibasic and 30% calcium carbonate.

These spray dried particles were coated with carnauba wax by a granulation technique. A ratio of 3:1 wax to particles was employed (225 g and 75 g). The procedure involved mixing the materials in a stem jacketed five quart Hobart bowl for 5 minutes at speed #1 (40-45 RPM). Then with continued mixing, the bowl was heated to approximately 50°-60° C. for 2-4 minutes until a slightly soft granular consistency was achieved. The wax granulation was then discharged onto a piece of paper and allowed to cool. The product was then milled in a CRC Micromill and sieved in a CSC Scientific sieve shaker.

BIOADHESION MEASUREMENTS

The microcapsules produced by the procedure of Example 4 were subjected to in vitro bioadhesion measurements, utilizing the modified technique of Robinson previously described.

Bioadhesion experiments were carried out on the spray dried particles and wax coated microcapsules of Example 4, along with the appropriate controls, using rabbit stomach tissue as described previously. The uncoated particles and wax coated microcapsules were found to possess similar bioadhesion characteristics. Additionally, the microcapsules of the granulation method of Example 4 and those of the hot wax melt procedure of Example 2 were found to possess similar bioadhesion characteristics, probably due to the fact that both batches of microcapsules were milled, and some negatively charged carboxyl groups may extend outside the wax coating.

DISSOLUTION EXPERIMENTS

The bioadhesive microcapsules prepared by the process described in Example 4 were subjected to in vitro dissolution experiments, in order to determine the relative sustained release characteristics of these microcapsules, compared to those prepared in Examples 1-3.

In vitro dissolution experiments were carried out with an initial acid challenge in 25 ml deionized water. The microcapsules were added and the increase in pH was monitored as a function of time. The samples were thermostated at 37° C. in a shaking water bath at 37° C. Measurements of pH were made at various time-points.

Dissolution experiments were also conducted for the gel-loaded microcapsules of Example 4. The procedure for dissolution studies carried out on microcapsules in a gel was slightly different. In this case, 10 g of gel (containing approximately 300 mg of microcapsules) was weighed into a 50 ml Erlenmeyer flask. A second flask contained 10 mg lactic acid in 25 ml deionized water. Both flasks were equilibrated to 37° C., and the lactic acid solution was added to the gel slowly to start the experiment. The agitation levels employed were 60 revolutions per minute for the microcapsules alone and 120 rpm for the microcapsules in a gel. A higher agitation rate was utilized in the case of the gel, in order to obtain a more uniform sample.

Microcapsules were loaded into a gel (99% propylene glycol thickened with 1% Klucel HF or 92% polyethylene glycol 400 thickened with 8% polyethylene glycol 1450) by heating the propylene glycol or PEG 400 to 50°-60° C., and then adding the thickening agent with vigorous stirring until uniform. The microcapsules were then added with continuous mechanical stirring for approximately 3-4 minutes until uniform and subsequently allowed to cool.

An IBM AT personal computer was used to graph the data with the Sigmaplot graphic software packages of Lotus and/or Sigmaplot (Jandel Scientific, Sausalito, CA).

A Radiometer PHM 84 research pH meter was employed for pH measurements.

The dissolution experiments indicated that the compositions of Example 4, whether or not loaded into gel, exhibited excellent sustained release properties.

Since wax is relatively non-adhesive, it was expected that a higher ratio of wax to spray dried particles would render the microcapsules less adhesive. However, since wax is hydrophobic in nature, a higher sustained release effect would be expected at high ratios. Therefore, a trade-off in adhesiveness and sustained release was noted with varying ratios of wax to spray dried material.

An experiment was carried out to determine the effect of mesh size on the dissolution rate of the wax coated granulated microcapsules of Example 4. This experiment showed that smaller particle sizes yielded a more rapid dissolution rate, during the first 30 minutes of the experiment.

Additional dissolution studies were carried out on the microcapsules of Example 4, wherein small additions of lactic acid were introduced during the dissolution in order to determine if the microcapsules had residual buffer capacity. These experiments also simulate additions of carbohydrate after the initial carbohydrate charge that would produce additional lactic acid.

The results of four 1 mg additions of lactic acid, after the initial 10 mg charge, show that these bioadhesive microcapsules exhibit good buffer capacity.

SEM STUDIES

SEM studies showed that the spray dried (uncoated) material of Example 4 was spherical in nature, while the lyophilized material (uncoated) of Example 1 was granular. Both of the wax coated materials from lyophilized (Example 2) and spray dried (Example 4) materials were granular. Particle sizes obtained were as follows:

| | |
|---|---|
| Spray dried | 3-5 microns |
| Spray dried - granulated/wax coated | 100 microns |
| Lyophilized | 400 microns |
| Lyophilized - hot melt wax coating | 700 microns |

Mapping experiments showed that the elements potassium, phosphorous, calcium, and sulphur were about equally dispersed in the spray dried and lyophilized materials.

All of the above-described compositions of the invention provide useful microcapsules which exhibit excellent bioadhesive properties, and permit the sustained release of an active agent over a 60-90 minute period of time. The microcapsules may be incorporated into a suitable delivery system to facilitate delivery of the active agents, such as basic salts, to the oral cavity or other physical location.

The invention being thus described, it will be obvious that the same may be varied in may ways. Such variations are not to be regarded as a departure from the spirit and scope of the invention and all such modifications are intended to be included within the scope of the following claims.

What is claimed is:

1. A composition of matter comprising bioadhesive microcapsules said microcapsules, being bioadhesive to the oral cavity and having anti-caries activity and consisting essentially of on a solid weight basis 1) about 1% or greater of a mixture of approximately equal amounts of xanthan gum and locust bean gum, 2) at least about 4% of a substantially water-soluble bulking agent selected from the group consisting of gelatin, hydrocolloids, glycerin, methylcellulose, polyvinylpyrrolidone, sodium carboxymethylcellulose, whey solids, and mixtures thereof, and 3) about 4.5% or greater of an active buffering agent selected from the group consisting of potassium phosphate dibasic, calcium carbonate, sodium potassium dibasic, sodium bicarbonate, ammonium bicarbonate, potassium carbonate, magnesium carbonate, calcium phosphate tribasic, sodium sesquicarbonate, ammonium carbonate, tetrasodium pyrophosphate, calcium hydroxide, sodium hydroxide, potassium hydroxide and mixtures thereof.

2. The composition of claim 1, wherein said bulking agent comprises gelatin.

3. The composition of claim 1, wherein said buffering agent comprises potassium phosphate dibasic.

4. The composition of claim 1, wherein said buffering agent comprises calcium carbonate.

5. The composition of claim 1, wherein said buffering agent comprises potassium phosphate dibasic and calcium carbonate.

6. The composition of claim 1, wherein said microcapsules are coated with a wax selected from the group consisting of animal waxes, vegetable waxes, mineral waxes, synthetic waxes and mixtures thereof.

7. The composition of claim 6, wherein said wax comprises carnauba wax.

8. The composition of claim 6, wherein said wax coating includes calcium carbonate.

9. The composition of claim 1, wherein said bioadhesive microcapsules are incorporated into a delivery system.

10. The composition of claim 9, wherein said delivery system comprises a gel.

11. The composition of claim 9, wherein said delivery system comprises a center-filled chewing gum.

12. The composition of claim 9, wherein said delivery system comprises a pressed mint.

* * * * *